United States Patent [19]
Bellouin et al.

[11] 4,094,188
[45] June 13, 1978

[54] APPARATUS FOR MONITORING THE APPLICATION OF A FORCE TO A SOLID BODY

[75] Inventors: François C. Bellouin, Mennecy; Jean G. Dremierre, Ballancourt sur Essonne, both of France

[73] Assignee: Societe Nationale des Poudres et Explosifs, France

[21] Appl. No.: 749,253

[22] Filed: Dec. 10, 1976

[30] Foreign Application Priority Data

Dec. 16, 1975  France .................... 75 38474

[51] Int. Cl.² ............................................ G01N 3/42
[52] U.S. Cl. .................................. 73/81; 73/141 R
[58] Field of Search ............ 73/81, 83, 141 R, 150 A, 73/105

[56] References Cited

U.S. PATENT DOCUMENTS

| 3,877,297 | 4/1975 | Oesterle | 73/81 |
| 3,956,924 | 5/1976 | Hansen et al. | 73/81 |

Primary Examiner—Jerry W. Myracle
Attorney, Agent, or Firm—Bucknam and Archer

[57] ABSTRACT

An apparatus for controlling the application of a force to a solid body, and, in particular, for measuring this force, displaced at constant velocity from its point of application, or for measuring the displacement of the point of application of the force, regarded as being constant, or for measuring this force, displaced at a constant velocity from its point of application, after application, during a predetermined period, of a constant force in the opposite direction, comprises: a measuring contact piece, designed to move into contact with the solid body; means for guiding this contact piece; actuating means for causing the contact piece to apply a continuously variable force to the solid body; and a dynamometric cell, fitted between the contact piece and the actuating means, for continuously measuring the force applied between the measuring contact piece and the solid body, the cell being provided with means for transmitting a signal representing the said force. The actuating means comprise means for imparting to the measuring contact piece a movement, which varies linearly with time, relative to the solid body, these means comprising a rotary motor associated with a screw and nut system.

16 Claims, 7 Drawing Figures

APPARATUS FOR MONITORING THE APPLICATION OF A FORCE TO A SOLID BODY

The present invention relates to an apparatus for controlling the application of a force to a solid body, and, in particular, for measuring this force, displaced at constant velocity from its point of application, or for measuring the displacement of the point of application of the force, regarded as being constant, or for measuring this force, displaced at a constant velocity from its point of application, after application, during a predetermined period, of a constant force in the opposite direction.

The invention also relates to various systems exemplifying the use of such apparatus, particularly a penetrometer or instrument for measuring the micro-hardness of materials.

The known apparatuses of the kind defined above are specifically used most frequently in penetrometers. It is known that the micro-hardness of a material such as a vulcanized rubber or a Propergol is determined by the depth of penetration of a blunt-ended needle into the material under the application of a predetermined force during a predetermined period. Provided that certain standard requirements are met, the micro-hardness can then be ascertained from the measured depth by simply reading it off from a table.

The use of this apparently simple procedure nevertheless entails considerable operating difficulties. If the displacements of the needle can be measured with precision by means of known devices of the comparator type, it is essential to be able to determine precisely the point at which penetration commences, that is to say the precise moment at which the needle enters into contact with the material and at which the load should be applied. Known apparatuses operate manually in the sense that it is the operator who, by optical or electrical means, determines when the needle makes contact, and who then applies the load. There is every evidence that this constitutes an important reason for the non-reproducibility of measurements, particularly if it is borne in mind that the load should be applied without impact.

The ability of the operator to determine when the needle moves into contact with the solid body is rendered considerably more unlikely in the case of very rough materials. In such cases it is known to make use of a pressure-applying cylinder which surrounds the needle and retains the sample in position, but which masks the point of the needle. Furthermore, measurements at the extreme edges of the specimen become impossible.

An object of the present invention is to provide an apparatus which, particularly when used in a penetrometer, enables the time of initial contact between the needle and the material to be detected, and the load to be applied to the needle without human intervention, thus providing excellent reproducibility in the measurements.

According to the invention, the apparatus for controlling the application of a force to a solid body, and, in particular, for measuring this force, displaced at constant velocity from its point of application, or for measuring the displacement of the point of application of the force, regarded as being constant, or for measuring this force, displaced at a constant velocity from its point of application, after application, during a predetermined period, of a constant force in the opposite direction, comprises: a measuring contact piece, designed to move into contact with the solid body; means for guiding this contact piece; actuating means for causing the contact piece to apply a continuously variable force to the solid body; and a dynamometric cell, fitted between the contact piece and the actuating means, for continuously measuring the force applied between the measuring contact piece and the solid body, this cell being provided with means for transmitting a signal representing the said force, which apparatus is characterized in that the actuating means comprise means for imparting to the measuring contact piece a movement, which varies linearly with time, relative to the solid body, these means comprising a rotary motor associated with a screw and nut system.

The presence of this dynamometric cell makes it possible, in particular, to detect with precision and perfect reproducibility, the moment when the contact piece makes contact, since said cell obviates the need for the operator to determine this.

It should be stated that the forces applied between the measuring contact piece and the solid body should be regarded here as having an algebraic value, that is to say that they may tend to embed the contact piece in the solid body as well as to separate it therefrom, thus providing, for example, an adhesivity measurement.

Similarly, the forces have envisaged are not limited to single forces, but may also designate couples. The displacement of the point of application should then be regarded as being an angular displacement.

The dynamometric cell comprises means for transmitting a signal representing the force applied between the measuring contact piece and the solid body. Thus, the force applied can be displayed, or this signal can be used for some control operation.

In a particular embodiment of the invention, the rotary motor associated with a screw and nut system is a step-by-step motor. The means for actuating the measuring contact piece also comprise an electric impulse generator for controlling said motor. Thus the rotary movement of the motor is converted into translatory movement of the measuring contact piece.

The screw and nut system preferably comprises a device for taking up play in such manner as to enable successive forces to be applied in opposite directions, during one and the same test, without introducing errors.

In an embodiment of the invention designed, in particular, to apply a constant force and to measure the displacement of the point of application of this force, for the purpose, for instance, of measuring the micro-hardness of a material, the apparatus comprises regulating means, responsive to the signal emitted by the dynamometric cell, for controlling the actuating means for the measuring contact piece, and means for counting the impulses emitted by this generator.

In another form of the apparatus of the invention, designed in particular to measure a force, having a constant velocity of displacement from its point of application, with a view, for instance, to determining the thickness of a coating layer applied to a solid body having a greater hardness than that of the coating, the apparatus comprises means for automatically controlling the impulse generator so as to impart a constant displacement velocity to the measuring contact piece, and means for twice deriving, in relation to time, the signal emitted by the dynamometric cell.

In a further embodiment of the invention, designed particularly for measuring a force, having a constant velocity of displacement from its point of application, after application, during a predetermined period, of a constant force in the opposite direction for the purpose, for example, of determining the adhesivity of the material, the apparatus comprises the elements of the two previous embodiments and, in addition, means for reversing the operating direction of the motor for actuating the measuring contact piece.

Other features and advantages of the invention will emerge from the following detailed description.

In the annexed drawings, provided by way of non-limiting examples.

Figure 1:
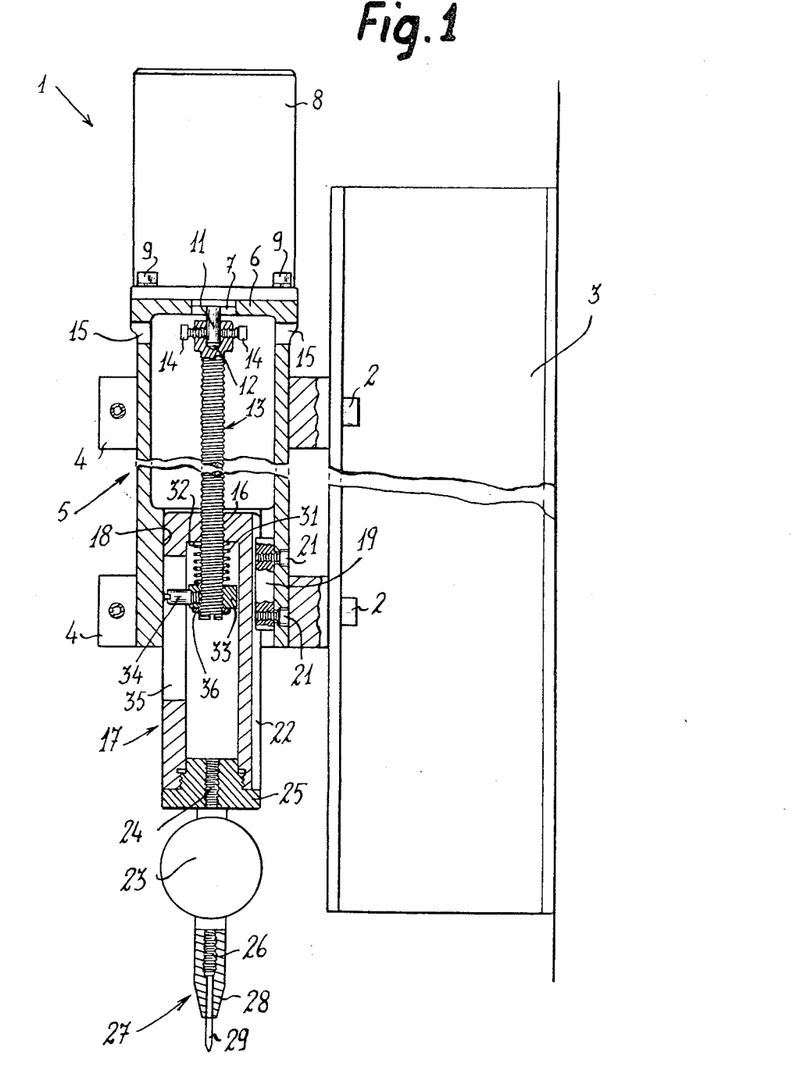
FIG. 1 is a part-sectional and part-diagrammatic view of an apparatus in accordance with the invention.

Referring to FIG. 1, the apparatus in accordance with the invention comprises a mechanical assembly 1, solidly connected by screw-bolts 2 to a suitable support 3 which is in turn firmly secured to a wall or workbench.

The screw-bolts 2 are screwed into two collars 4 of the assembly 1 which surround and grip a substantially cylindrical case 5 closed at its top by a cover plate 6 having an opening 7 at its centre.

A step-by-step electric motor 8 is secured to the cover plate 6 by screw-bolts 9 so that its shaft stub 11 extends through the opening 7 into the interior of the case 5.

A bore 12 formed in a screw 13 engages the shaft stub 11 and is secured thereto by screws 14 which can be tightened and loosened through openings 15 in the case 5. The screw 13 co-operates with an axial female screw-thread 16 formed at the upper part of a column 17 mounted to slide freely and without clearance in a bore 18 of the case 5. The column 17 is held against rotation by a key 19 secured to the case 5 by screws 21 and co-operating with a longitudinal channel 22 formed in said column.

A dynamometric cell 23 carries a screw-threaded rod 24 which is screwed into an end-piece 25 which is in turn screwed into the bottom of the column 17. This cell carries another screw-threaded rod 26 on to which is screwed a measuring contact piece 27, which, in the example here described, comprises a needle-holder 28 in which is fitted a needle 29.

The cell 23, illustrated diagrammatically, does not itself form part of the invention; it is of a commercially available type and should have a measuring range in the order of ± 2 daN, so as to be able to operate under both tensile and compressive load; it should also be very rigid. A suitable cell would be, for example, the type FC cell made in France by Société SEDEME. Whatever its type, the cell used should be designed to emit an electric signal dependent upon the force applied to it.

A play take-up device comprises a spring 31 compressed between the inner upper face 32 of the column 17 and a nut 33 screwed on to the screw 13. Screwed on to the side of the nut 33 is a pip 34 which engages in a longitudinal slot 35 formed in the column 17 so that the nut 33 is held against rotation.

It will be appreciated that when the screw 13 is caused to rotate, the column 17 and the nut 13, held against rotation, are displaced at the same speed, and that the spring 31 remains compressed to a constant extent, thus ensuring take-up of the play between the female screw-thread 16 and the threads of the screw 13. In the example described, the pitches of the screw 13 and of the motor 8 are such that one pitch of the motor 8 corresponds to a displacement of the screw of 5 $\mu$ mm.

The length of the slot 35 is so selected as to enable the compression of the spring 31 to be regulated in the best possible manner.

A pin 36 fitted in the lower end of the screw 13 prevents the nut 33 from accidentally falling out in the event of incorrect handling of the apparatus.

Finally, the outer surface of the column 17 and the surface of the bore 18 are precision machined so as to form an adequate guide.

When operating, the above-described apparatus permits the continuous measurement of the force applied by the measuring contact piece 27 to a specimen of material placed below it, in terms both of tensile force and compressive force, the velocity of the point of application of this force being kept constant by suitably controlling the motor 8 by means of a control device such as that to be described hereinafter.

The apparatus also permits a constant effort to be applied by a regulating device such as that described below and using the signal emitted by the cell 23; furthermore the apparatus is able to measure the displacement of the point of application of this force by counting the threadturns of the motor 8.

Finally, because of the presence of the play takeup device, this apparatus permits the carrying out of a test which combines the two previous ones and using forces applied in opposite directions to each other.

Figure 2:
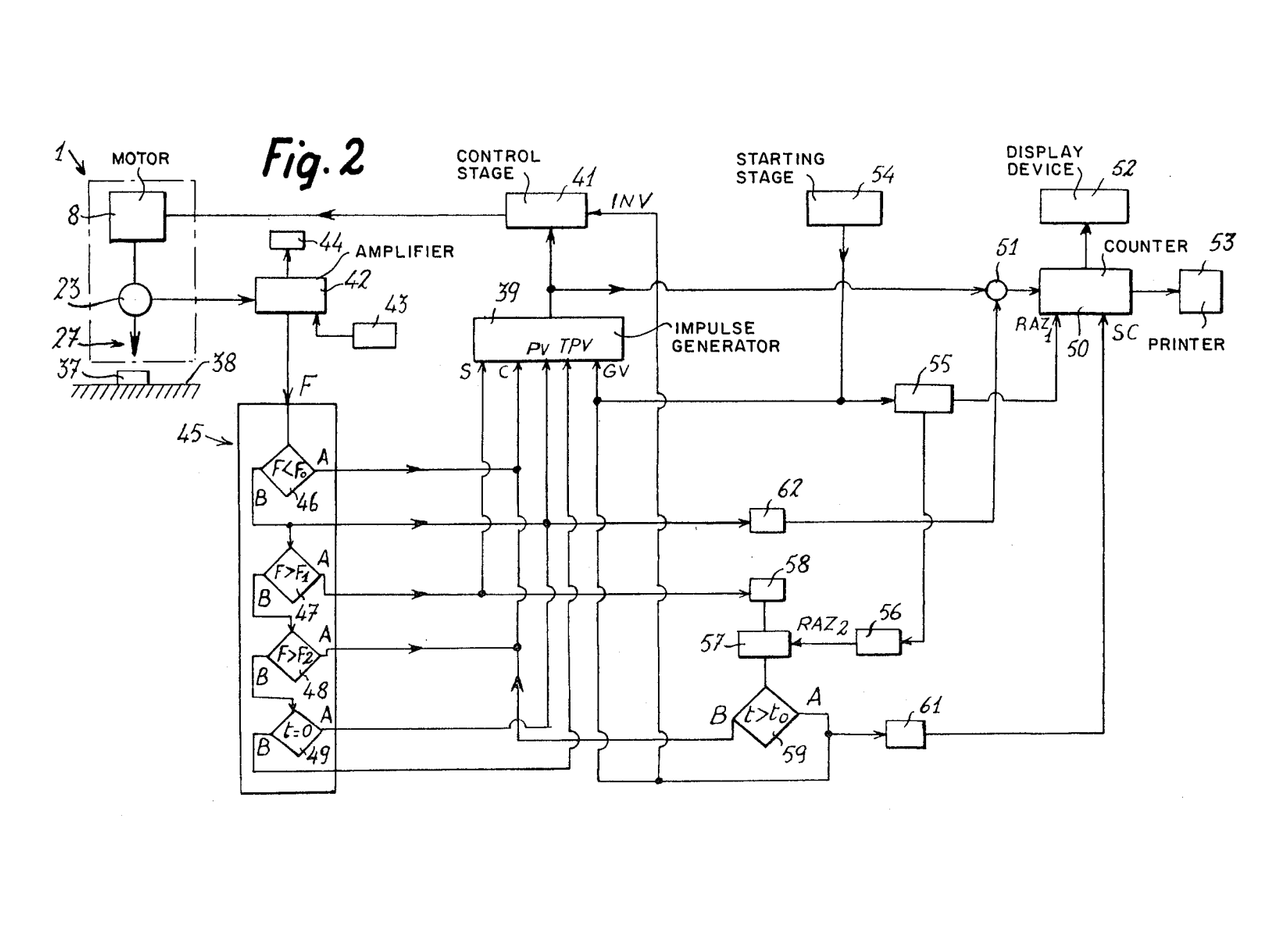
FIG. 2 is a block diagram illustrating the whole of the system for measuring the micro-hardness of a material.

There will now be described, by reference to FIG. 2, a system in accordance with the invention for measuring the micro-hardness of materials, which system represents a first application of the above-described apparatus.

A specimen 37 of the material to be tested is placed on a bench 38 below the measuring contact piece 27 of the apparatus 1 illustrated in FIG. 1. An impulse generator 39, having three predetermined frequencies, controls the motor 8 through a control stage 41 of known type.

In the example to be described, the frequencies of the generator 39 are 400 Hz, 100 Hz and 10 Hz, which, bearing in mind what has been explained above, correspond to velocities of the contact piece 27 of 2 mm/s, 500 $\mu$ mm/s and 50 $\mu$ mm/s, respectively.

The impulse generator 39 has five control inputs, namely:

an input GV for causing emission at high frequency,
an input PV for causing emission at the medium frequency,
an input TPV for causing emission at low frequency,
an input C for causing the generator to continue to emit at the frequency at which it is emitting at the time, and
an input S to stop emission.

The control stage 41 comprises an additional input INV to cause the generator to reverse the direction of movement of the motor 8, and it is programmed to turn the motor 8 through precisely 1000 screw-threads as from the moment when the input INV is activated.

The output signal from the cell 23 is applied to an amplifier 42, supplemented by an adjusting stage 43, which delivers a signal to, on the one hand, an analogue output device 44, and on the other hand, a monitor 45 comprising three logic output comparators 46, 47 and 48, designed to compare the force signal F, emitted by the cell 23, with each of three predetermined values $F_0$, $F_1$ and $F_2$, which will be particularized below.

Each of the comparators 46, 47 and 48 is designed to deliver, in an exclusive manner, two signals A and B corresponding respectively to the replies "yes" and "no" to the conditions $F < F_0$, $> F_1$ and $F > F_2$, respectively.

The signals A from the comparators 46 and 48 are sent to the input C of the generator 39, and the output A from the comparator 47 is sent to the input S of said generator.

The outputs B from the comparators 46 and 47 are passed respectively to the inputs of the later comparators 47 and 48. Furthermore, the output B from the comparator 46 is passed to the input PV of the generator 39.

Finally, the output B from the comparator 48 is passed to the input of a fourth comparator 49 designed to divert this signal to the input PV or to the input TPV of the generator 39, depending upon a parameter $t$ which will be defined below and is zero in the one case and not zero in the other.

The generator 39 also delivers pulses to a counter 50 through an authorization gate 51. The counter 50 is connected to a display device 52 and to a printer 53 and it has a zeroing input RAZ1 and an input SC, which when energized starts the counting operation.

A manual starting stage 54 is connected to a control stage 55 connected, on the one hand, to the input RAZ 1 of the counter 50 and on the other hand, to a subsequent control stage 56 connected through its output to an input RAZ 2 of a timer 57, the start-up of which is controlled by a stage 58 which receives the signal A from the comparator 47.

The manual starting stage 54 again passes signals to the input GV of the impulse generator 39.

The output from the timer 57 is applied to a comparator 59 designed to compare the time $t$, measured by the timer, with a reference time $to$, and to deliver through two different channels, a signal A if $t > to$, and a signal B if $t < to$. It is this same time $t$ which concerns the comparator 49.

The signal A from the comparator 59 is applied, in parallel to the input GV of the impulse generator 39, to the input INV of the control stage 41 and to a control stage 61 connected to the input SC of the counter 50.

The signal B from the comparator 59 is applied to the input C of the impulse generator 39.

Finally, the gate 51 is opened by a control stage 62, which is itself responsive to the signal B from the comparator 56.

The mode of operation of the system detailed above will now be described on the basis of an actual example, so that at the same time details will be given of a method of using this system for measuring the micro-hardness of materials.

Assuming that the measuring contact piece 27 is in its upper position, a specimen of the material, the micro-hardness of which it is required to measure, is placed on the bench 38. This material may be a resilient one such as a vulcanized rubber or a Propergol, and it will be recalled that the principle upon which the measurement of micro-hardness is based consists in measuring the depth of penetration of a point into the material by the application of a given force during a given period.

Actuation of the manual starting stage 54, on the one hand, starts up the motor 8 at great speed by energizing the output GV of the impulse generator 39 and on the other hand, returns the counter 50 and the timer 57 to zero through the control stages 55 and 56.

The measuring contact piece then moves downwards towards the speciment 37 at a velocity of 2 mm/s. The dynamometric cell 23 is not subjected to any force, so that the signal F is zero, and consequently, lower than the threshold value $F_0$. The comparator 46 then emits the signal A which instructs the generator 49 to continue, and it does not emit the signal B, so that the gate 58 remains closed, and the impulses are not counted.

As soon as the contact piece 27 makes contact with the speciment 37, the cell 23 is subjected to an increasing force. Conveniently, contact is established when the force signal F reaches a predetermined value $F_0$, which is equal to 0.2 Newton. At this moment, the comparator 46 emits the signal B which opens the gate 51, and the impulses begin to be counted by the counter 50 and shown on the display device 52. At the same time this signal B acts on the input PV of the generator 39 to produce a mean velocity of descent of 500 $\mu$ mm/s.

The contact piece 27, which in this instance comprises a blunt-ended needle 29, penetrates into the material until the force signal F reaches the region of the threshold values $F_1$ and $F_2$ which define the constant force which is the parameter of the test in question. These threshold values are 25 Newtons and 24 Newtons in this case, so that the constant force applied can be said to be 24.5 Newtons.

While this region is not reached, the comparators 47 and 48 deliver the signal B, but since the timer 57 has not yet started up, the time $t$ is zero. Consequently, the comparator 49 passes the signal B to the input PV of the generator 39, and the mean velocity continues to be applied.

When the upper value $F_1$ is reached, the comparator 47 delivers the signal A which causes stoppage of the motor 8 through the input S of the generator 39. At the same time, by way of the control stage 58, this signal A starts up the timer 57, and the time $t$ measured thereby is continuously compared with a predetermined time $to$ which is a parameter of the test and is in this case 5s.

The descent of the needle having been arrested, the material relaxes and the force applied to the cell 23 diminishes. When the signal F drops below the lower value $F_2$ of the regulating range, the comparator 48 emits the signal B, which is then diverted to the input TPV, since $t$ is no longer zero, so that the needle is therefore actuated at the low velocity of 50 $\mu$ mm/s.

The resultant penetration again causes increase in the signal F until the threshold value $F_1$ is reached and descent is arrested.

The arrest-low velocity penetration continues until the period, during which the test is to continue, has been reached, i.e., until the time $t$ exceeds the value $to$. At this moment the comparator 59 emits the signal A which, through the control stage 61, stops the counter 50 and causes the printer 53 to operate. At the same time, the signal A causes the motor 8 to turn at great speed and to reverse its direction, so that the needle 29 is lifted over a distance equivalent to one thousand thread pitches, i.e., 5 mm.

It should be mentioned that this device for lifting the needle and involving automatic reversal of the motor is not absolutely essential, in the present application, for carrying out the test, but that it simply represents a considerable extra facility.

At the moment when the counter 50 is stopped, its contents define the degree of penetration achieved and therefore represent an indication of the micro-hardness.

Determination of the moment of contact between the needle 29 and the material takes place automatically as a function of an objective criterion and does not require the personal judgment of the operator. On the other hand, the automatic control of the velocity of descent permits the needle to make contact with the material, and whatever the surface condition of the material no pressure-applying cylinder is necessary so that measurement can be made very close to the edges of the specimen. Finally, the very great rapidity with which the test can be carried out permits a very large number of measurements to be carried out at numerous points on the specimen in a reasonable time, particularly when use is made of a bench 38, the displacements of which are automatically controlled.

Measurements carried out on various raw rubbers gave the following results:

|  | Type of raw rubber | Micro-hardness (mm$^{-1}$) |
| --- | --- | --- |
| (I) | Butyl HT 1066 | 0.28 |
| (II) | BR 1220 | 0.23 |
| (III) | Butyl 218 | 0.28 |
| (IV) | Vistanex | 0.47 |

These results correspond to the values which these materials are generally regarded as having. These rubbers are produced by Esso (I, III, IV) and Shell (II).

Figure 3:
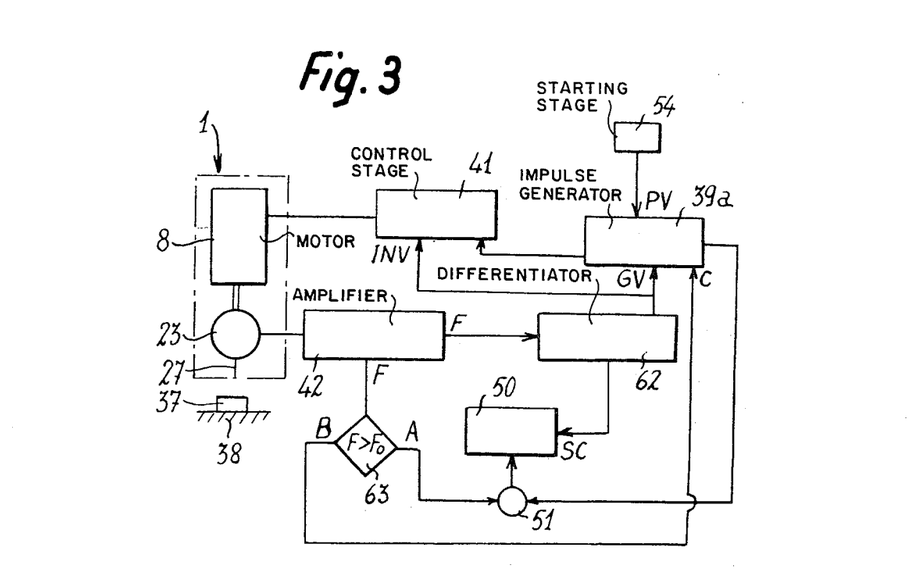
FIG. 3 is a block diagram illustrating the whole of the system for measuring the thickness of a coating.

There will now be described, by reference to FIG. 3, a system for measuring the thickness of a coating on a material having a hardness greater than that of the coating, this system constituting a second application of the apparatus illustrated in FIG. 3, this application consisting in measuring a force, moving at a constant velocity from its point of application.

This system comprises a certain number of stages identical to that described by reference to FIG. 2, which stages were not all shown in that Figure, so as to make it simpler.

The thickness-measuring system comprises the previously described apparatus 1, the motor 8 of which is actuated, through the control stage 41, by an impulse generator 39a, which may be identical to the generator 39, but which may also be simpler, in that, for example, the input TPV is not required since only the frequencies 100 Hz and 400 Hz are used in this thickness-measuring system. The generator 39a is connected at its output to a pulse counter 50.

The dynamometric cell 23 is connected to an amplifier 42, the output signal F of which is transmitted to a double differentiator 62 which produces a signal $(d^2F/dt^2)$, that is to say, the second derivative of the force signal F in relation to time.

The amplifier 42 again passes the signal F to a comparator 63 designed to pass a signal B to the input C of the generator 39a if the signal F is greater than a predetermined threshold value $F_0$, and emits a signal A in the contrary case for permitting opening of the gate 51 interposed between the generator 39a and the counter 50.

The double differentiator 62 is designed to take into account the occurrence of peak values of the signal $(d^2F/dt^2)$ which it produces, and to deliver at its output a logic signal when the second peak occurs. This logic signal is applied to the input GV of the generator 39a, to the input INV of the control stage 41, and to the input SC of the counter 50.

The manual starting stage 54 is connected to the input PV of the generator 39a and to the input RAZ 1 of the counter 50. To make the drawing clearer, this latter connection has not been illustrated.

Figure 4:
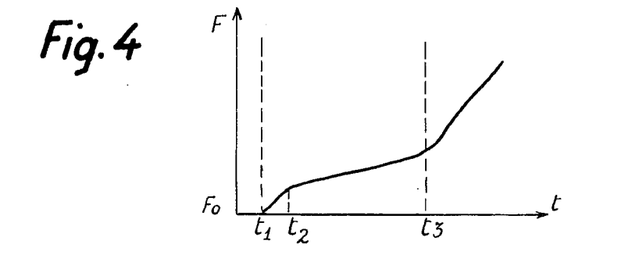
FIGS. 4 and 5 are curves designed to explain the operation of the system shown in FIG. 3.
Figure 5:
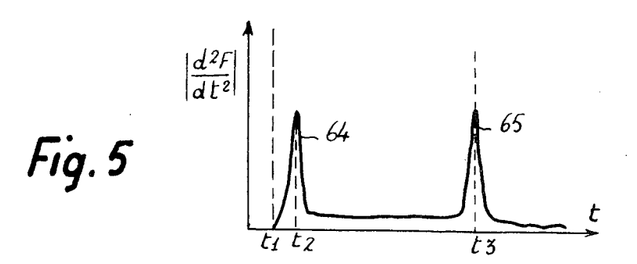

There will now be described, also by reference to FIGS. 4 and 5, the mode of operation of this system and, at the same time, a method of using it for the purpose of measuring the thickness of a coating layer.

In the example selected, the coated material is a rubber having a hardness of 65 Shore A units, and the coating is a rubber having a hardness of 20 Shore A units.

The specimen 27 is placed below the measuring contact piece 29 which here consists of a cylindrical needle 27 having a diameter of 0.6 mm.

By operating the manual starting stage 54, the impulse generator 39a is caused to emit impulses which have a frequency of 100 Hz and which, by way of the stage 41 and of the motor 8, cause the needle 27 to descend at a velocity of 500 µ mm/s. Since the force applied to the cell 23 is zero, the comparator 63 delivers a signal B which causes the generator 39a to continue not to deliver a signal A, so that the gate 51 remains blocked and the counter 50, reset to zero through the stage 54, does not start up.

When the needle 29 comes into contact with the specimen 37, the applied force increases suddenly, and this contact can be detected objectively when a threshold value $F_0$ of 0.2 Newton or another value of the same order has been passed.

When the threshold value has been passed, this causes the comparator 63 to oscillate, and thereafter this comparator emits the signal A which blocks the gate 51. Thus, as from the moment $t_1$ (FIG. 4) when the threshold value is passed, the counter 50 counts the impulses that come from the generator 39a.

The needle having passed through the surface layer at the moment $t_2$, penetration continues in correspondence with a force which increases more slowly (FIG. 4), so that at the moment $t_2$, the second derived signal $(d^2F/dt^2)$ exhibits a peak 64 (FIG. 5) corresponding to the change in rate of the variation of the force as a function of time.

As penetration proceeds, the needle encounters the harder covered material at the moment $t_3$ so that the variation in the force changes to a new rate which results in a new peak 65 in the curve of the second derived signal. FIG. 5 illustrates the absolute value of the second derived signal so that the two peaks 64 and 65 extend in the same direction.

When the second peak occurs, the double differentiator 62 emits a logic signal which, when applied to the input INV of the stage 41 and the input GV of the generator 39a, causes the needle to be lifted at the greater velocity of 2 mm/s and, when said logic signal is applied to the input SC of the counter 50, causes counting to stop. The contents of the counter at the moment $t_3$ thus represent the degree of penetration achieved between the moments $t_1$ and $t_3$, and therefore the thickness of the covering.

The system described, like the previous system, of course comprises a certain number of auxiliary stages such as display and printing devices which have not been mentioned here so as to shorten the explanation.

Figure 6:
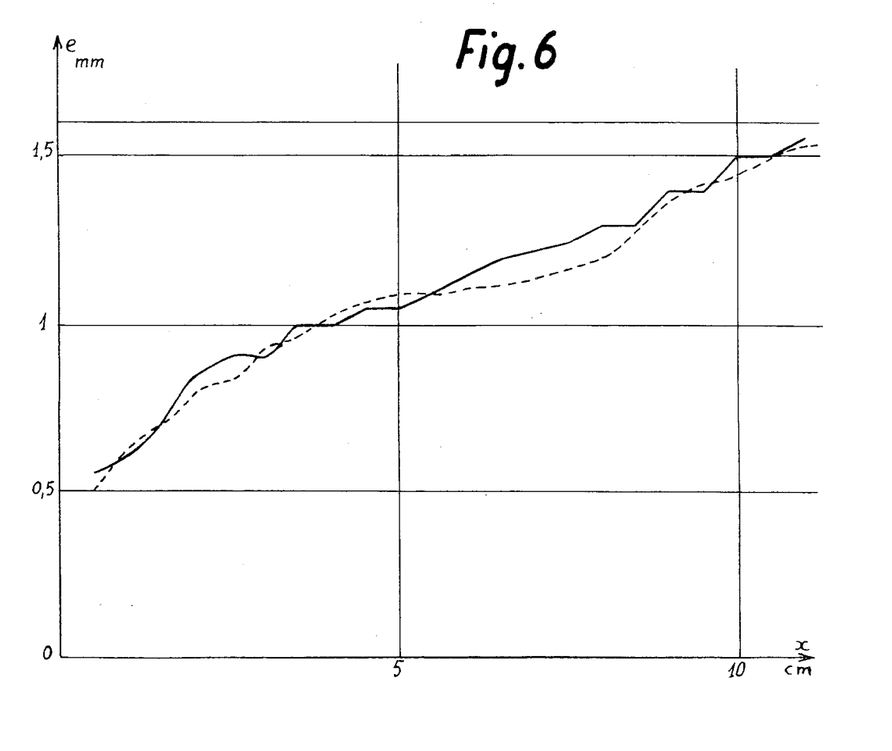
FIG. 6 is a measuring test diagram made with the aid of the apparatus in accordance with the invention.

FIG. 6 shows a graph relating to measurements made by means of a system in accordance with the invention on a specimen having a coating, the thickness of which was intentionally varied. The thickness of the coating is plotted against the point of measurement (x-axis). The broken-line curve relates to measurements carried out by means of the system, and the solid-line curve to measurements carried out by destroying the specimen. Very considerable coincidence will be observed, and the slight gaps that occurred could have been due just as much to the one system of measurement as to the other. It can be considered that the precision obtained is in the order of 0.1 mm for thicknesses of between 0.5 and 3 mm.

This system could be improved by a device described above by reference to FIG. 2, and the use of this device would result in the descent of the needle, prior to contact, taking place at a high velocity. The system could also be simplified by dispensing with the arrangement for the automatic controlled lifting of the needle, which arrangement in no way concerns the test proper and only constitutes a means for facilitating the use of the apparatus.

Figure 7:
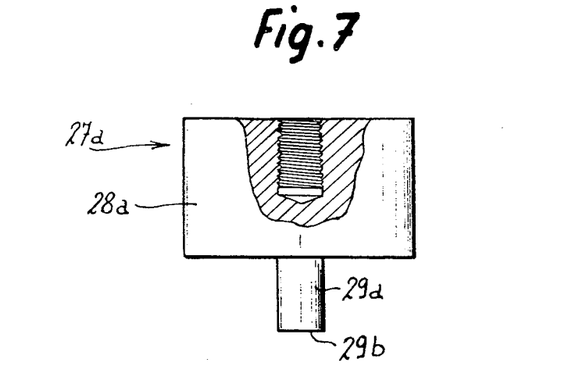
FIG. 7 is a sectional view of the measuring contact piece used for measuring adhesivity.

There will now be described, by reference to FIGS. 2 and 7, a system for measuring the adhesivity of a material, this system representing a third application of the apparatus described by reference to FIG. 1; this application consists in measuring a force which is displaced at a constant velocity from its point of application, after application, during a predetermined period, of a constant force in the opposite direction.

In its general outlay, this system is identical to that described by reference to FIG. 2. However, it differs slightly in that it comprises a measuring contact piece 27a (FIG. 7) comprising a block 28a, screwed on to the screwthreaded rod 26 of the dynamometric cell 23. This block 28a has a cylindrical stud 29a, the lower face 29b of which is polished. In the example here described, the diameter of the stud 29a is 5 mm.

Furthermore, the analogue output device 44 is preferably a recording device or, optionally, a crest voltmeter.

The mode of operation of the system is substantially the same as that of the system for measuring microhardness apart from just a few differences which relate to the method of carrying out operations and to the measuring procedure rather than to the system itself.

The sample 37 is firmly secured to the bench 38 in such a way that, in particular, it cannot be suddenly displaced. Then, the measuring contact element 27a is first caused to descend at high velocity, and following this it descends at medium velocity once contact has been established with the specimen; finally, it descends at low velocity when the force applied is within a regulating range $F_1$ to $F_2$. The values of the threshold $F_0$, defining contact, and of the forces $F_1$ and $F_2$ defining the constant applied force are again 0.2, 25 and 24 Newtons respectively. Similarly, the period $t_0$ during which this force is applied from the moment of contact is again 5 s.

When the period $t_0$ elapses, the needle is again raised at a velocity of 2 mm/s, but in this case the measuring contact piece adheres to the specimen so that the dynamometric cell 23 measures an increasing tensile force. When this tensile force reaches a sufficiently high value to cause separation, this separation takes place and the cell suddenly measures a zero force. If the maximum tensile force is read off on the recorder 44, this gives an adhesivity index.

A certain number of stages in the system, in particular the counter 50 and the associated stages, do not operate in this case and could be dispensed with.

On the other hand, certain elements which were only optional in the previously described systems are essential in the present one, namely, a dynamometric cell which is able to measure tensile as well as compressive forces, controlled automatic means for lifting the contact piece, and the play take-up device which, while simply being very useful when the force applied is directed in one direction only, becomes essential when the direction of the force is changed.

Measurements carried out at 20° C on fresh cuts of raw rubber gave the following results:

| Type of raw rubber | Adhesivity ($g/cm^2$) | |
| --- | --- | --- |
| Butyl HT 1066 | 2145 | (I) |
| | 2135 | |
| BR 1220 | 205 | |
| | 235 | (II) |
| | 230 | |
| Butyl 218 | 1170 | |
| | 1230 | (III) |
| | 1110 | |
| Vistanex 80 | 515 – 395 | |
| | 500 – 610 | (IV) |

The designations correspond to the commercial names of rubbers produced by Esso (I, III, IV) and Shell (II).

The differences in the measurements relating to specimen II are due to the irregular surface condition of the cut. Also, specimen IV exhibited considerable lack of uniformity and this explains the scatter in the results.

Taking these factors into account, it can be said that the measurements exhibit excellent reproducibility.

A fourth application of the apparatus 1 may consist in the provision of a system for measuring the roughness of a surface or the porosity of a material. Such a system is identical to that used for measuring adhesivity, except that the measuring contact piece is in this case a suction cup which is applied to the specimen and permits leakage of varying magnitude depending upon the degree of roughness or porosity, and causing separation under tensile forces of varying magnitude.

It will be obvious that the embodiments described are provided simply by way of example and that numerous modifications are possible within the framework of the invention. Thus, for example, the systems illustrated in the block diagrams could be designed in any other equivalent manner. Also, in the apparatus 1, the motor 8 could be a continuous-current motor operating at constant voltage, displacement being measured by integration of the current.

We claim:

1. Apparatus for controlling the application of a force to a solid body, and, in particular, for measuring this force, displaced at constant velocity from its point of application, or for measuring the displacement of the point of application of the force, regarded as being constant, or for measuring this force, displaced at a constant velocity from its point of application, after application, during a predetermined period, of a constant force in the opposite direction, comprising: a measuring contact piece, designed to move into contact with the solid body; means for guiding this contact piece; actuating means for causing the contact piece to apply a continuously variable force to the solid body; and a dynamometric cell, fitted between the contact piece and the actuating means, for continuously measuring the force applied between the measuring contact piece and the solid body, this cell being provided with means for transmitting a signal representing the solid force, and wherein the actuating means comprise means for imparting to the measuring contact piece a movement, which varies linearly with time, relative to the solid body, these means comprising a rotary motor associated with a screw and nut system and the apparatus comprises an impulse generator having a plurality of predetermined selectible frequencies for actuating said motor.

2. Apparatus according to claim 1 wherein the rotary motor is an electric step-by-step motor.

3. An apparatus for measuring the thickness of a coating applied to a material having a hardness greater than that of the coating, according to claim 2, which comprises an impulse generator having at least one predetermined frequency for actuating the step-by-step motor, means for detecting the passage, beyond a predetermined threshold value, of the signal emitted by the dynamometric cell, and means for calculating the second derived signal in relation to time, means for measuring the time that elapses between passage beyond said threshold value and the occurrence of a second peak in the signal representing the said second derived signal.

4. The apparatus according to claim 3 wherein the measuring contact piece is a cylinder having a diameter of approximately 0.6 mm.

5. The apparatus according to claim 3 which additionally comprises means for successively measuring tensile and compressive forces in one and the same operation, these means comprising a play take-up device.

6. Apparatus according to claim 1 which comprises means for successively measuring tensile and compressive forces in one and the same operation, these means comprising a play take-up device.

7. An apparatus according to claim 1 for measuring the micro-hardness of materials wherein said impulse generator has a plurality of predetermined selectible frequencies for actuating the step-by-step motor at corresponding speeds, means for automatically selecting said frequencies in dependence upon the value of the signal emitted by the dynamometric cell, means for automatically detecting contact between the measuring contact piece and a specimen, means for automatically stopping the motor after a predetermined time, and means for counting the impulses emitted by the generator.

8. An apparatus according to claim 7 wherein the measuring contact piece comprises a needle fitted in a needle-holder.

9. The apparatus according to claim 7 which additionally comprises means for successively measuring tensile and compressive forces in one and the same operation, these means comprising a play take-up device.

10. An apparatus for measuring the adhesivity or roughness of a material according to claim 1 which comprises: means for successively measuring tensile and compressive forces in one and the same operation, these means comprising a play take-up device; an impulse generator having a plurality of selectible predetermined frequencies for actuating a step-by-step motor at corresponding speeds; means for automatically selecting said frequencies in dependence upon the value of the signal emitted by the dynamometric cell; means for automatically detecting entry into contact of the measuring contact piece and the specimen; means for automatically reversing the direction of movement of the motor after a predetermined period; and means for measuring the maximum tensile force applied by the measuring contact piece.

11. An apparatus according to claim 10 wherein the measuring contact piece has a polished face for applying to the specimen.

12. An apparatus according to claim 11 wherein the measuring contact piece comprises a suction cup designed to be applied to the specimen.

13. A method of measuring the micro-hardness of a material which comprises:
   a. securing a specimen of the material to a support below a movable measuring contact piece,
   b. causing the measuring contact piece to descend rapidly by application of a force until it comes into contact with the specimen,
   c. causing the measuring contact piece to penetrate the specimen at medium velocity and, at the same time, count-down of time is begun,
   d. when a predetermined value for the force applied by the measuring contact piece to the specimen is reached, arresting and resuming penetration alternately at low velocity, so that the force applied remains within a range corresponding substantially to the above-mentioned predetermined force and,
   e. when a predetermined time has elapsed following contact between the measuring contact piece and the specimen, measuring the penetration achieved, the degree of this penetration providing an indication of the microhardness of the material.

14. A method according to claim 13 wherein the contact established between the measuring contact piece and the material is considered to have taken place when the force applied is in the order of 0.2 Newton, the substantially constant applied force is in the order of 25 Newtons, the predetermined period of the test is in the order of 5s, and the velocities of descent of the measuring contact piece are in the order of 2 mm/s 500 $\mu$ mm/s and 50 $\mu$ mm/s.

15. A method of measuring the thickness of a coating applied to a material having a hardness greater than that of the coating which comprises:
   a. causing a measuring contact piece to penetrate into a sample of the coated material at a constant velocity,
   b. measuring the time that elapses between the entry into contact of the contact piece with the coating and the occurrence of the second peak in the second derived signal in relation to the duration of the force applied to the measuring contact piece.

16. A method of measuring the adhesivity or roughness of a material which comprises:
   a. applying a measuring contact piece to the material under a predetermined force and during a predetermined period,
   b. applying a tensile force to the measuring contact piece to cause it to be displaced at a constant velocity in the direction opposite to that in which the said force is applied,
   c. measuring the maximum tensile force at the moment when the measuring contact piece is separated from the specimen.

* * * * *